US00PP22459P3

(12) United States Plant Patent
Maddalena

(10) Patent No.: US PP22,459 P3
(45) Date of Patent: Jan. 17, 2012

(54) **VARIETY OF *RUBUS* PLANT NAMED 'BP1'**

(50) Latin Name: *Rubus idaeus*
Varietal Denomination: BP1

(76) Inventor: Grisenti Maria Maddalena, Trento (IT)

( * ) Notice: Subject to any disclaimer, the term of this patent is extended or adjusted under 35 U.S.C. 154(b) by 0 days.

(21) Appl. No.: 12/800,021

(22) Filed: May 6, 2010

(65) Prior Publication Data

US 2011/0277194 P1 Nov. 10, 2011

(51) Int. Cl.
*A01H 5/00* (2006.01)

(52) U.S. Cl. ..... Plt./204

(58) Field of Classification Search ..... Plt./204
See application file for complete search history.

*Primary Examiner* — June Hwu

(74) *Attorney, Agent, or Firm* — The Webb Law Firm

(57) ABSTRACT

A new and distinct cultivar of *Rubus* plant named 'BP1' having large, easy to pick fruits with a long shelf life.

13 Drawing Sheets

Botanical classification: *Rubus idaeus.*
Varietal denomination: 'BP1'.

BACKGROUND OF THE INVENTION

The present invention comprises a new and distinct cultivar of *Rubus idaeus* known by the varietal name 'BP1'.

The new cultivar was discovered in October of 2006 in Trento, Italy as part of a planned breeding program. The purpose of the breeding program was to develop better primocane raspberries with bigger fruits. The new variety is the result of a cross between raspberry variety 'Polka' (female parent, unpatented) and raspberry variety 'Tulameen' (male parent, unpatented). The new variety is similar in habit to 'Polka', but is easier to pick than 'Polka'. Further, the new variety is similar to 'Tulameen' in fruit form in flavor, but 'BP1' is a primocane raspberry instead of a floricane raspberry. The new variety was first asexually reproduced by root cuttings in Trento, Italy in 2007. Continued observations of asexual reproductions of the new variety have confirmed that the distinguishing features of this new cultivar come true, remain stable, and are retained through successive propagations.

The following traits are determined to be basic characteristics of this new cultivar which distinguish this raspberry plant as new and distinct when compared to other raspberry varieties known to the breeder:

1. Conical fruits;
2. Big drupelets;
3. Excellent shelf life; and
4. Easy to pick Further, in comparison to raspberry plant 'Sugana' (U.S. Plant Pat. No. 21,357), the new variety has more flowers per cane and the fruit is easier to pick.

DESCRIPTION OF THE DRAWINGS

The accompanying photographic drawings illustrate the new cultivar, with the colors being as nearly true as possible with color illustrations of this type.

DESCRIPTION OF THE NEW PLANT

Figure 1:
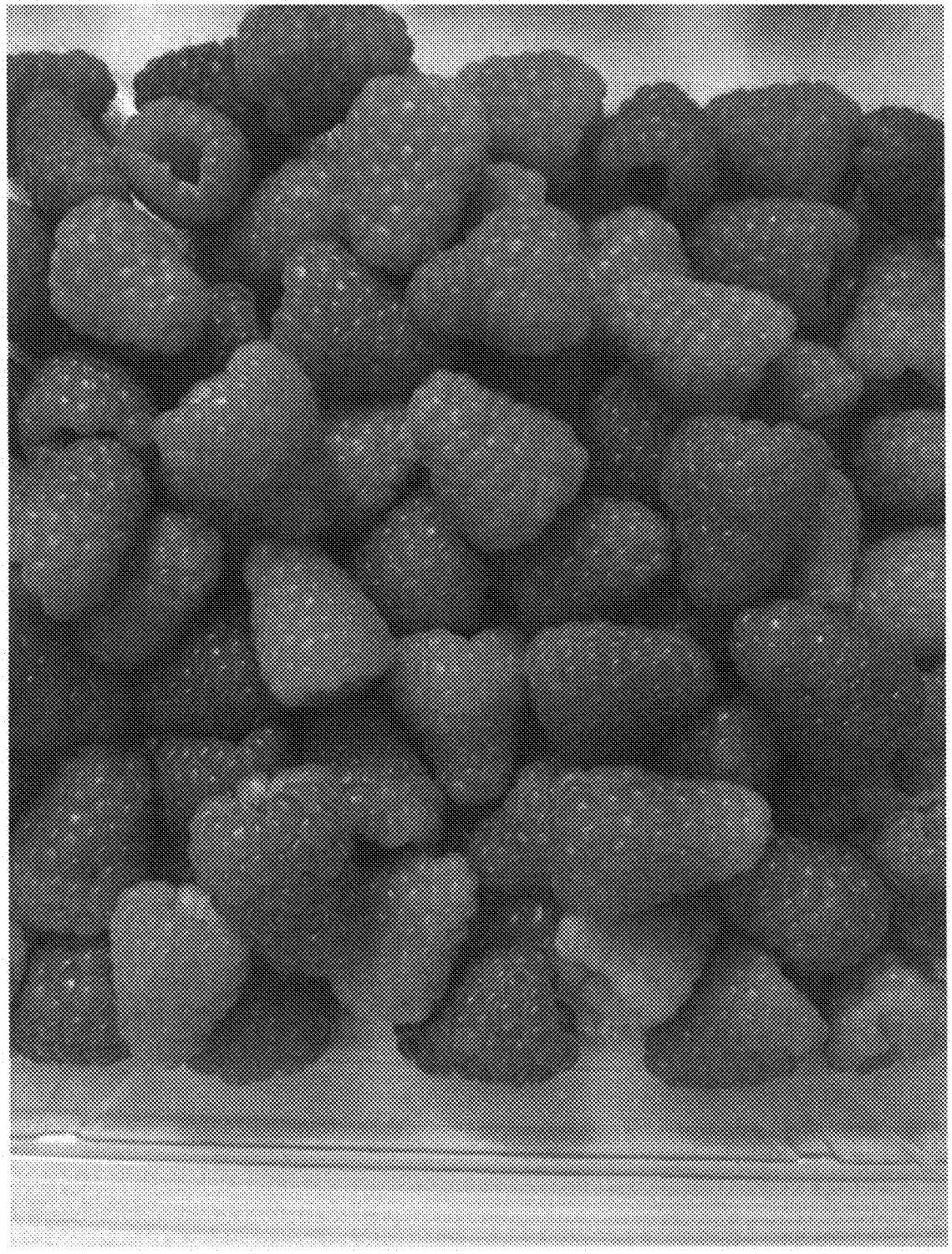
FIG. 1 illustrates the fruits of the new variety.
Figure 2:
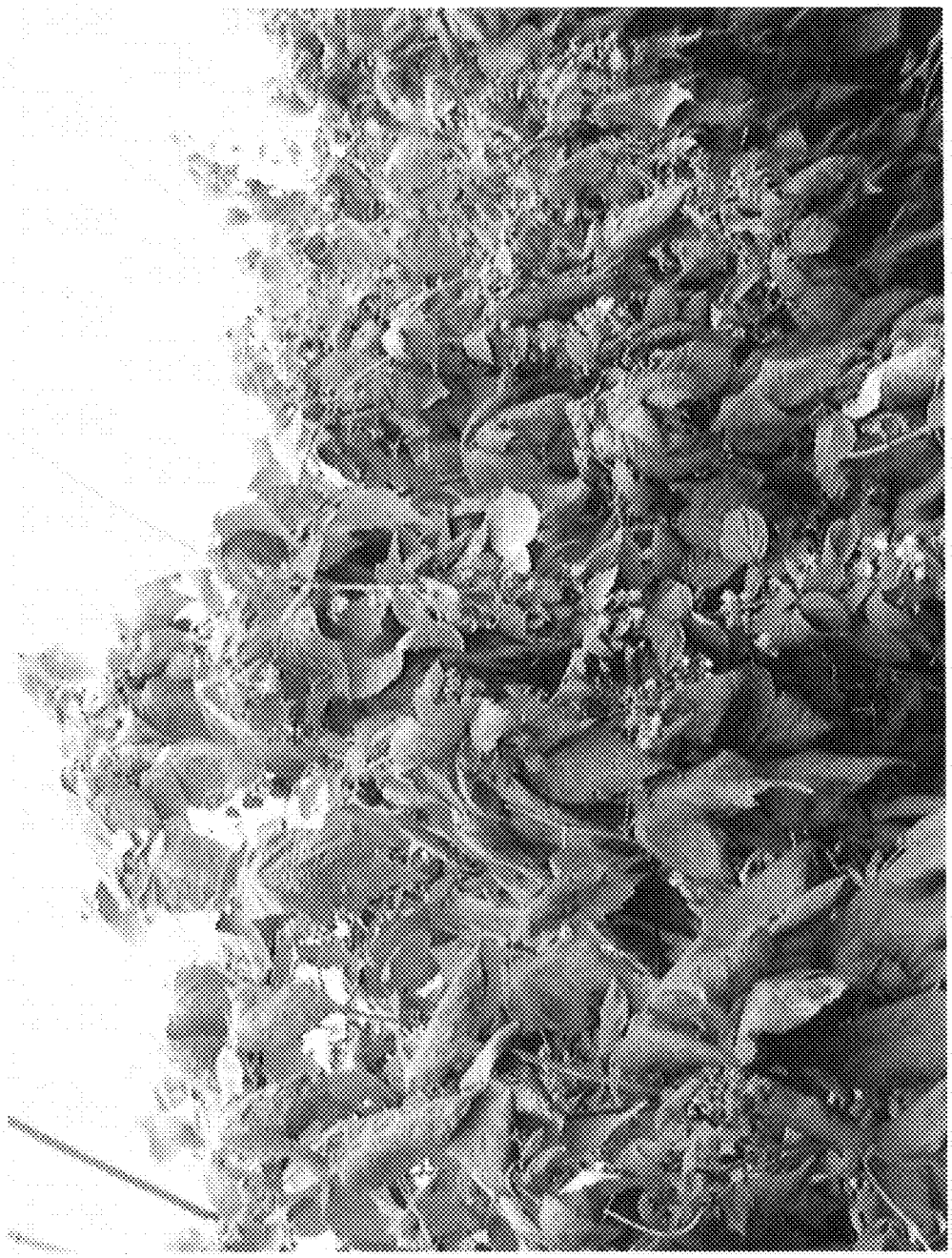
FIG. 2 is a photograph of multiple plants of the new variety.
Figure 3:
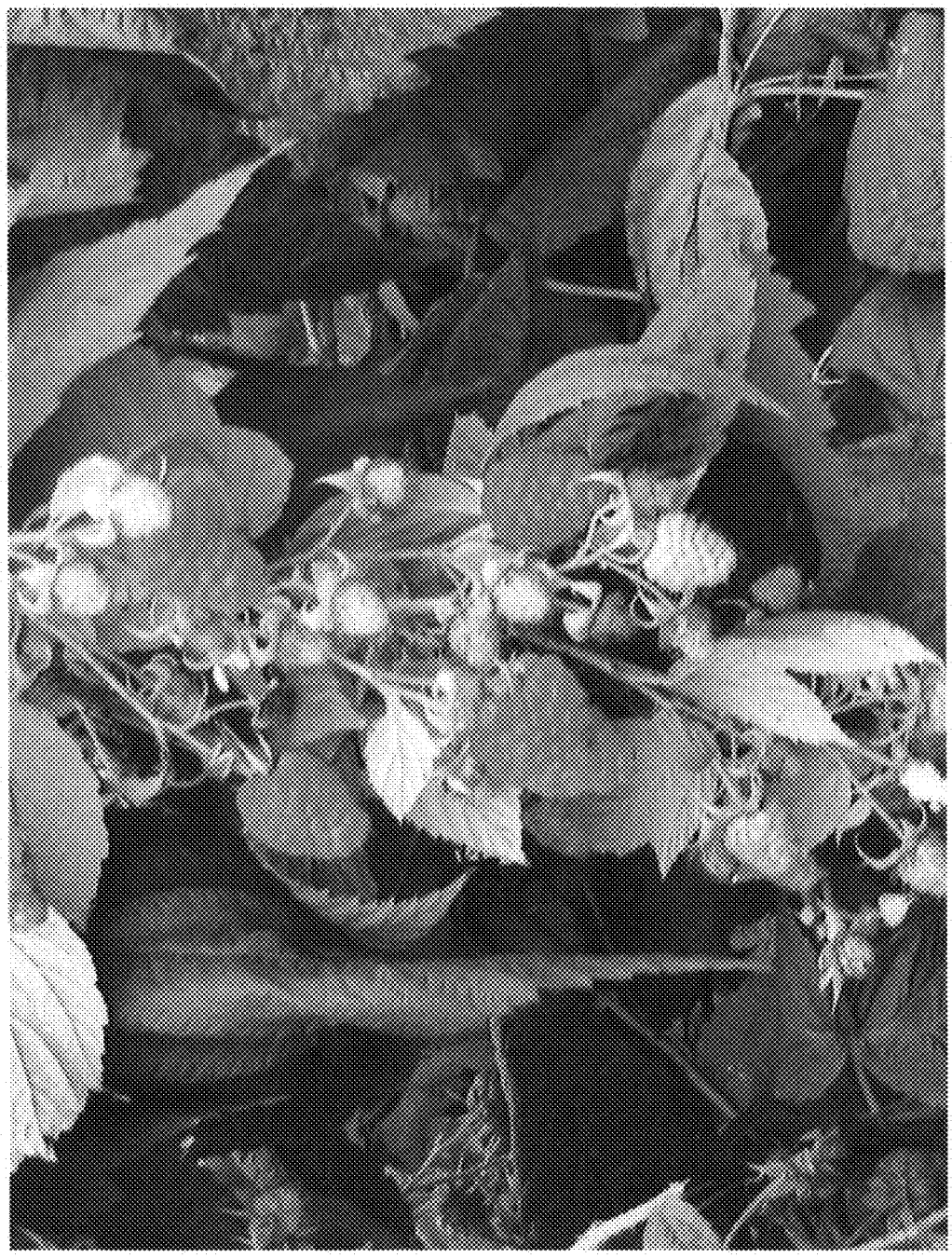
FIGS. 3 and 4 illustrate the fruits and leaves of the new variety.
Figure 4:
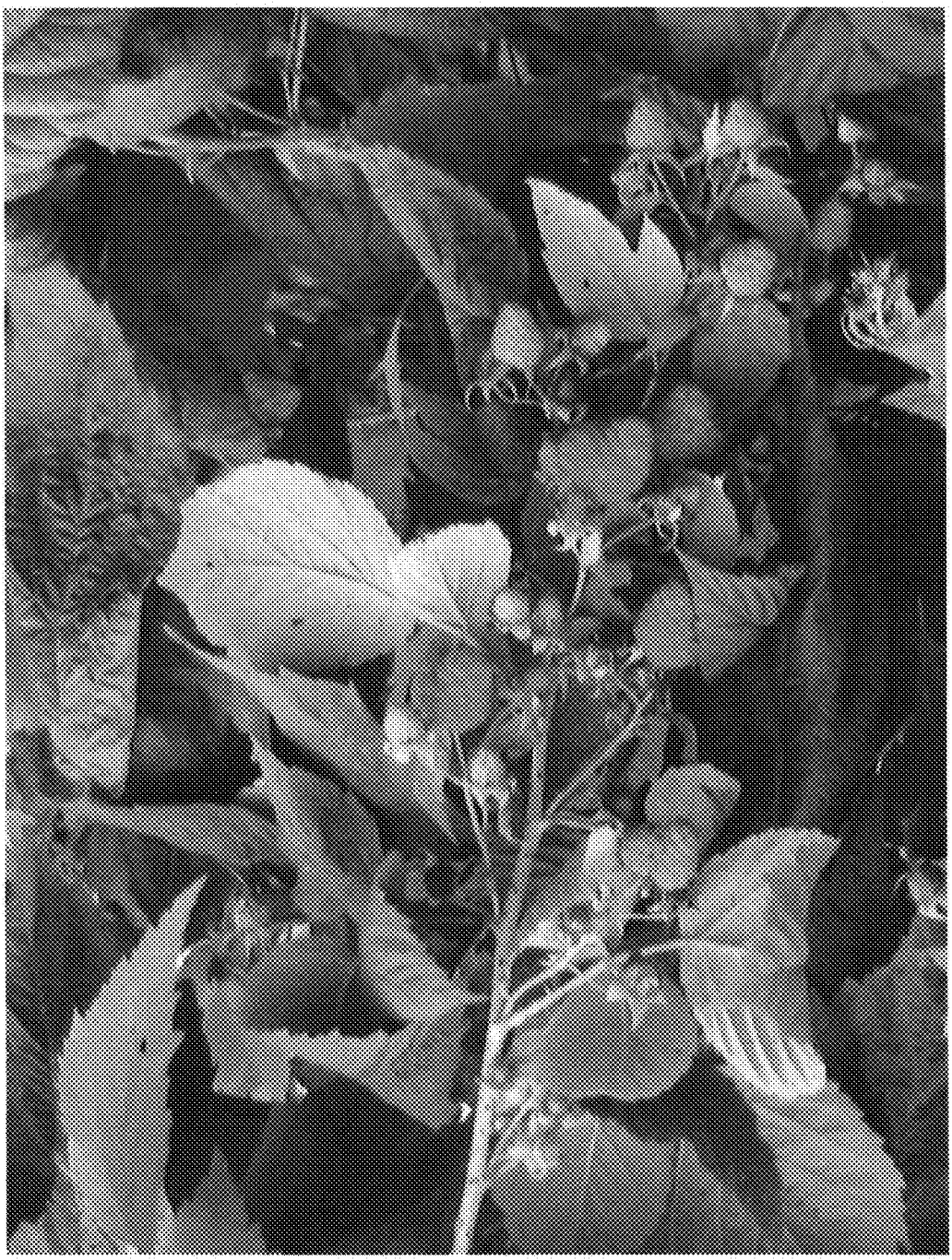
Figure 5:
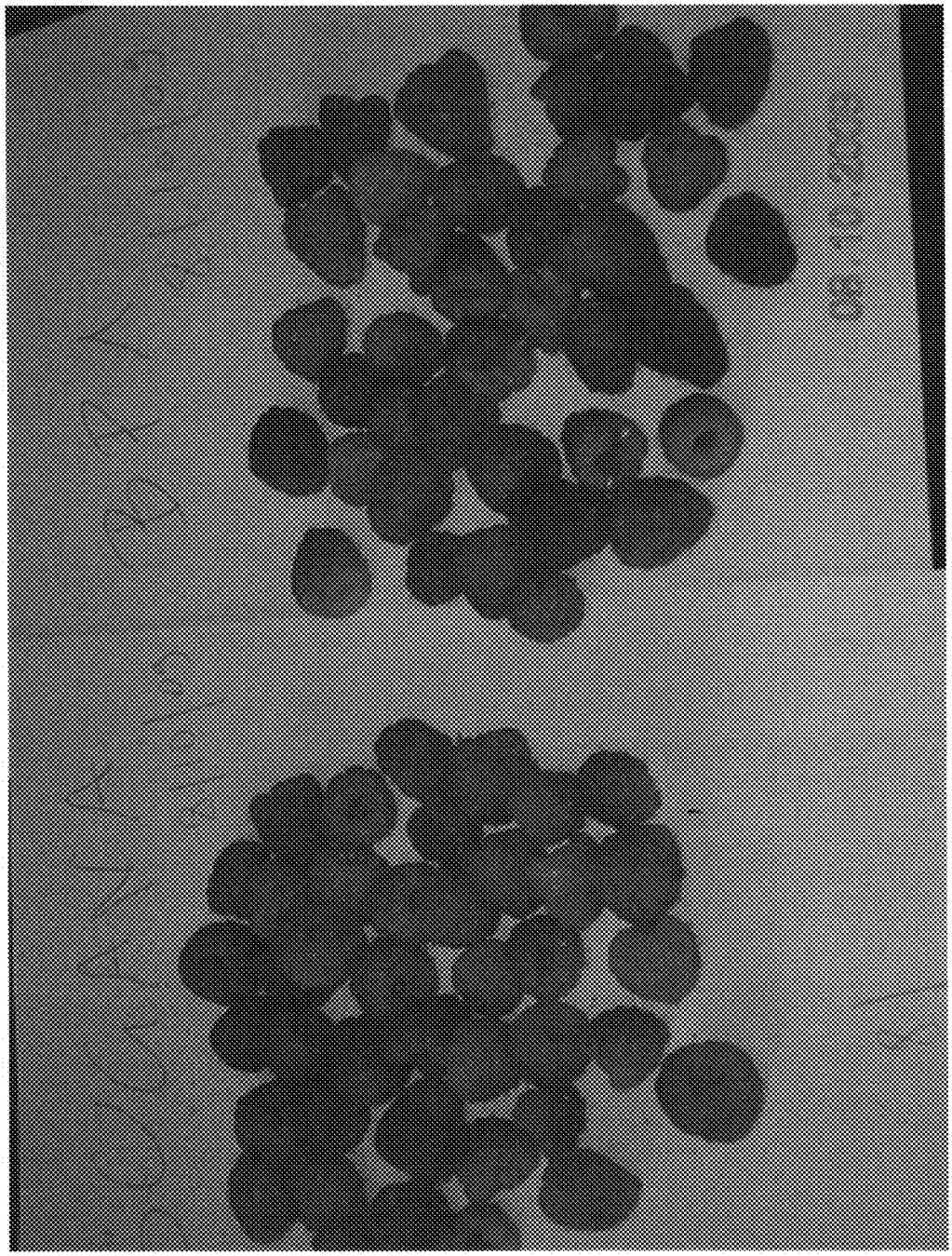
FIG. 5 is a comparison of the fruits of 'Sugana' versus the fruits of 'BP1'.
Figure 6:
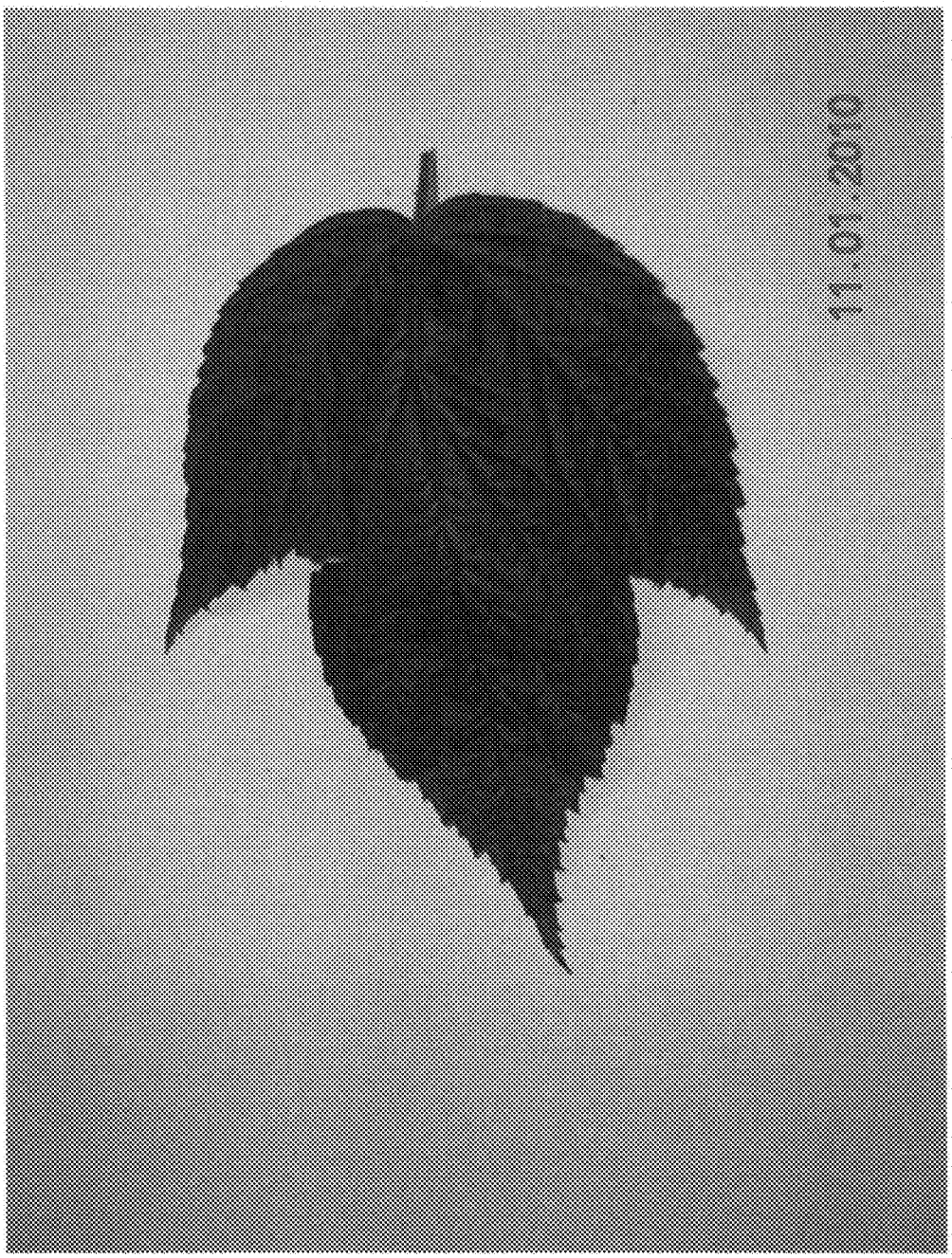
FIG. 6 illustrates the upper surface of a young leaf of the new variety.
Figure 7:
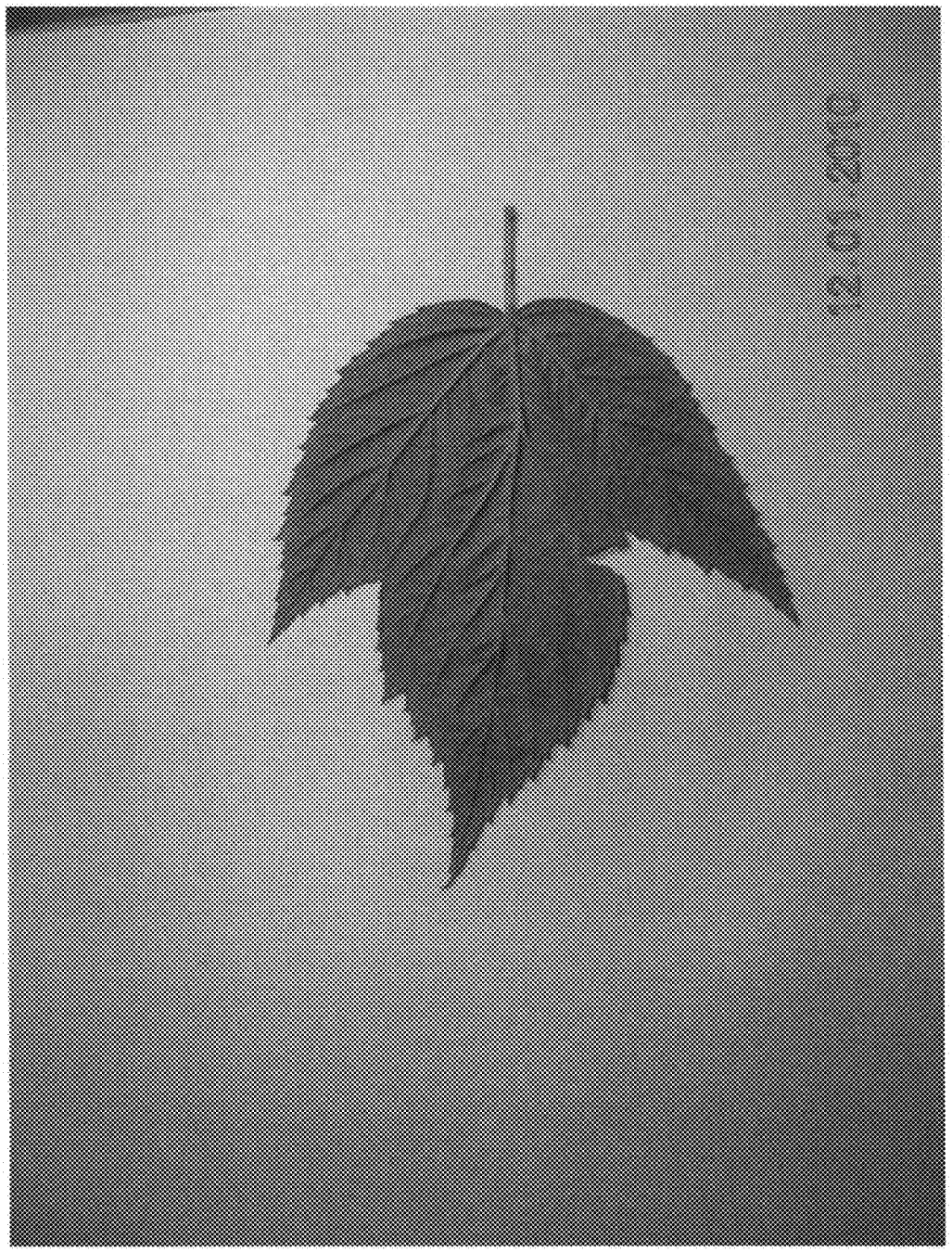
FIG. 7 illustrates the lower surface of a young leaf of the new variety.
Figure 8:
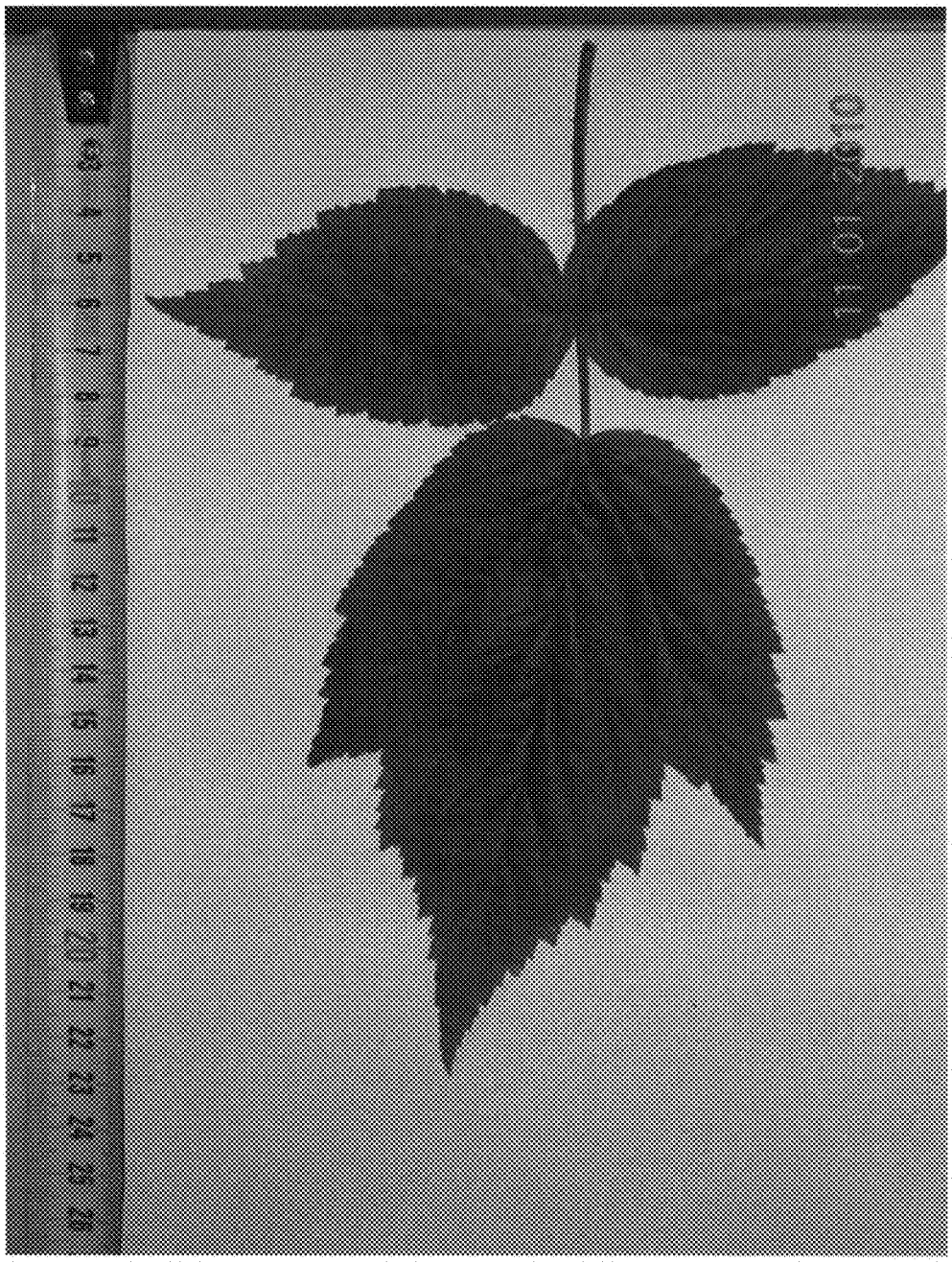
FIG. 8 illustrates the upper surface of a mature leaf of the new variety.
Figure 9:
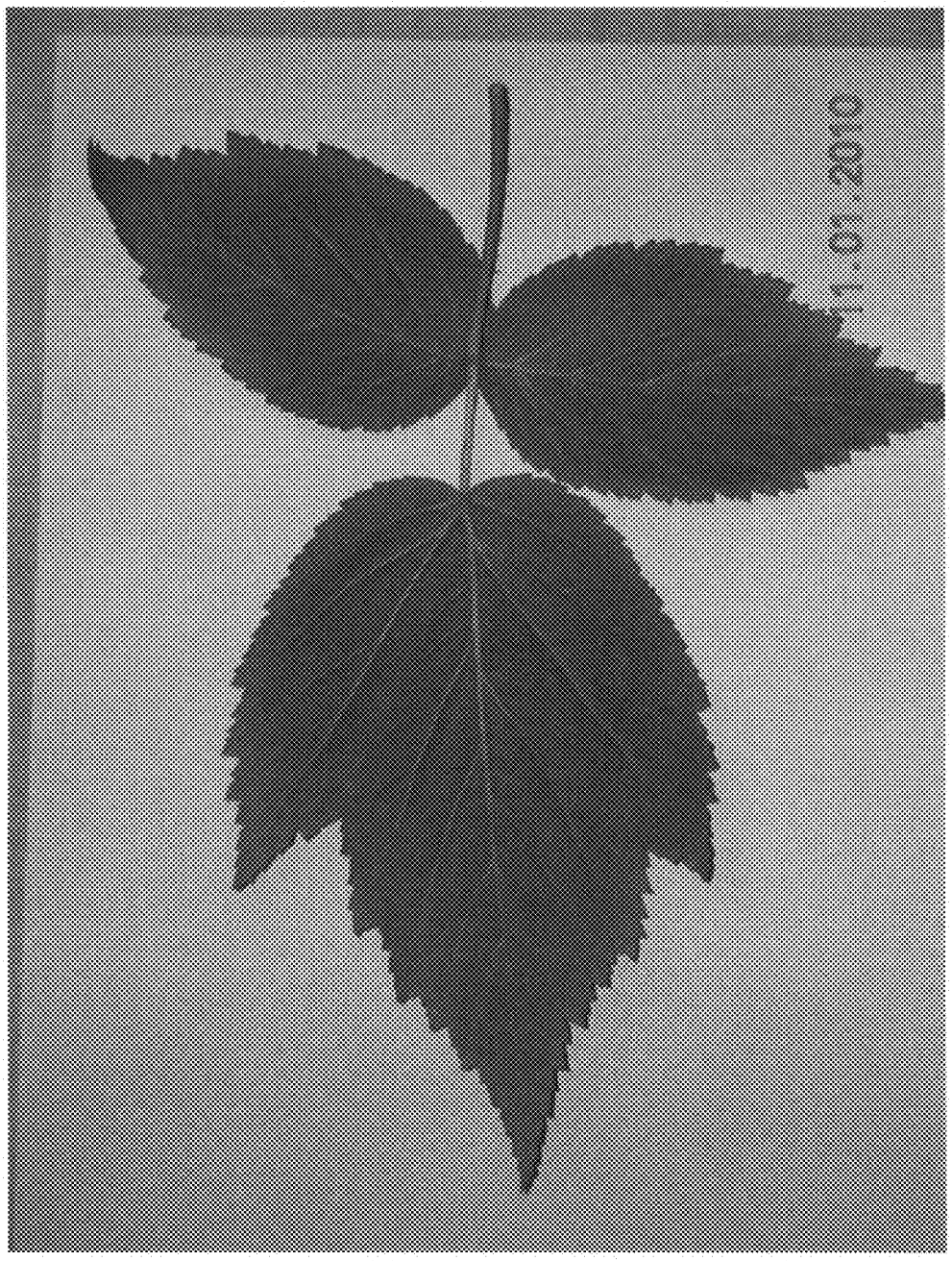
FIG. 9 illustrates the lower surface of a mature leaf of the new variety.
Figure 10:
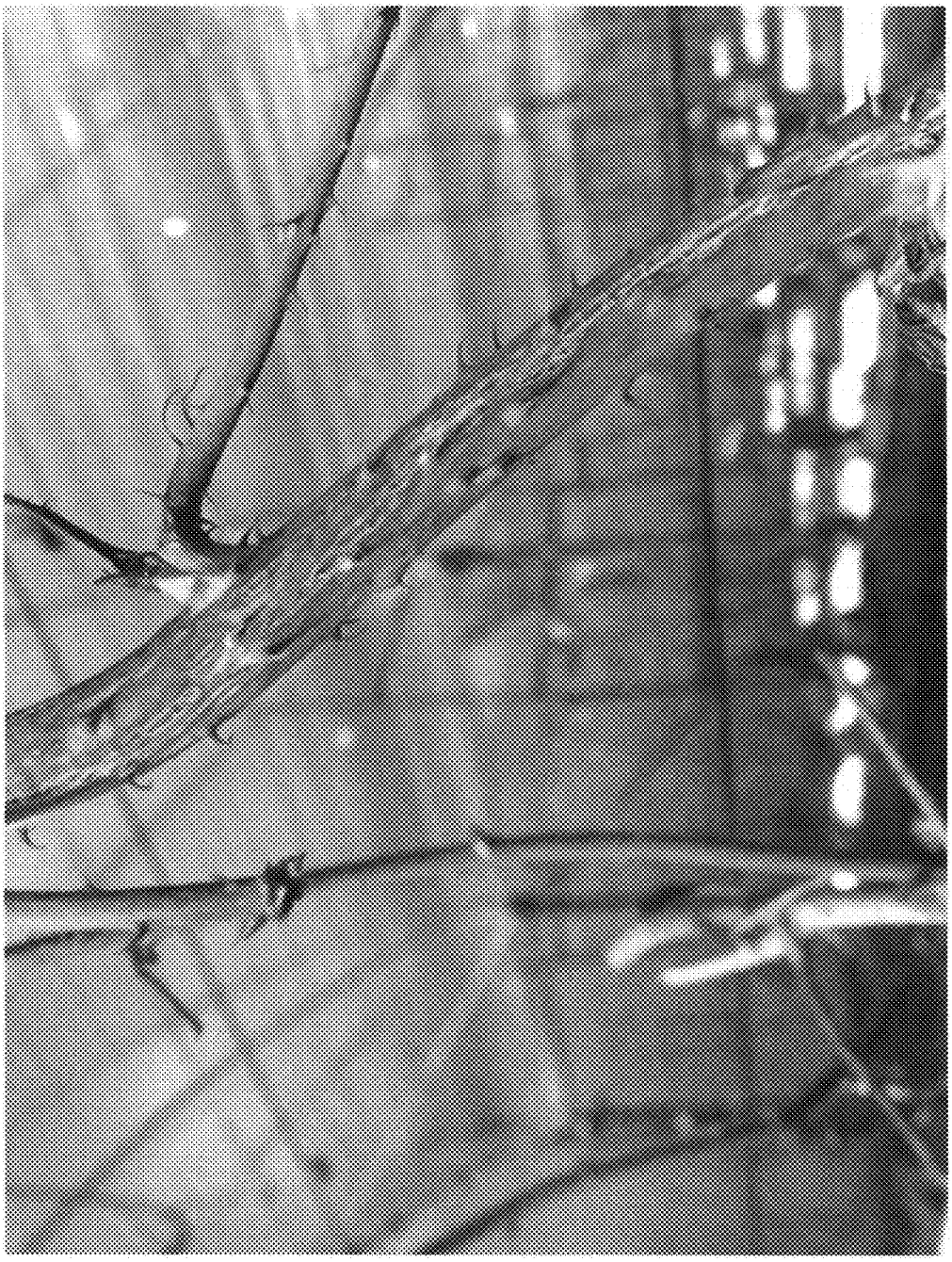
FIG. 10 illustrates the thorns of 'BP1'.
Figure 11:
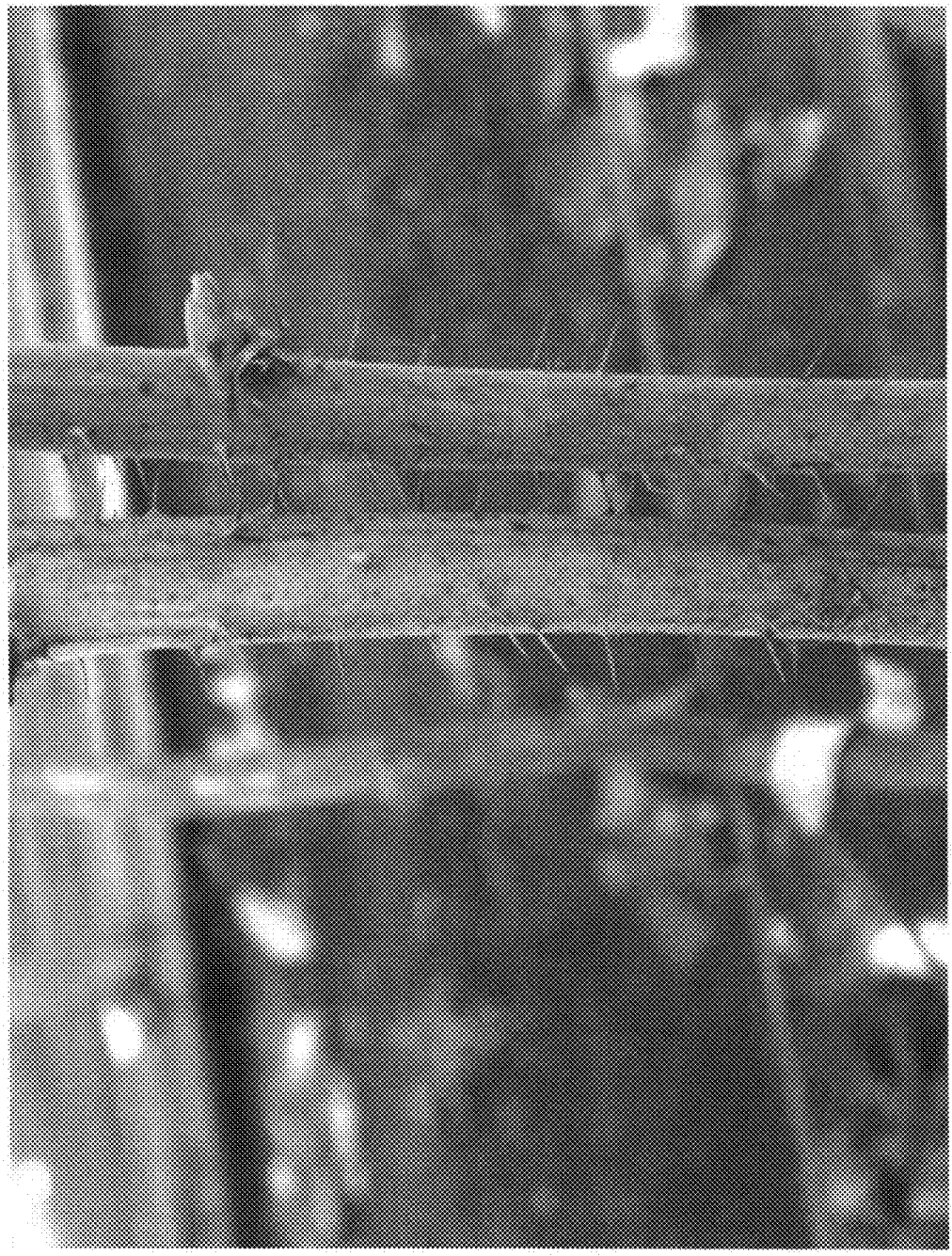
FIG. 11 illustrates the thorns of 'Sugana'.
Figure 12:
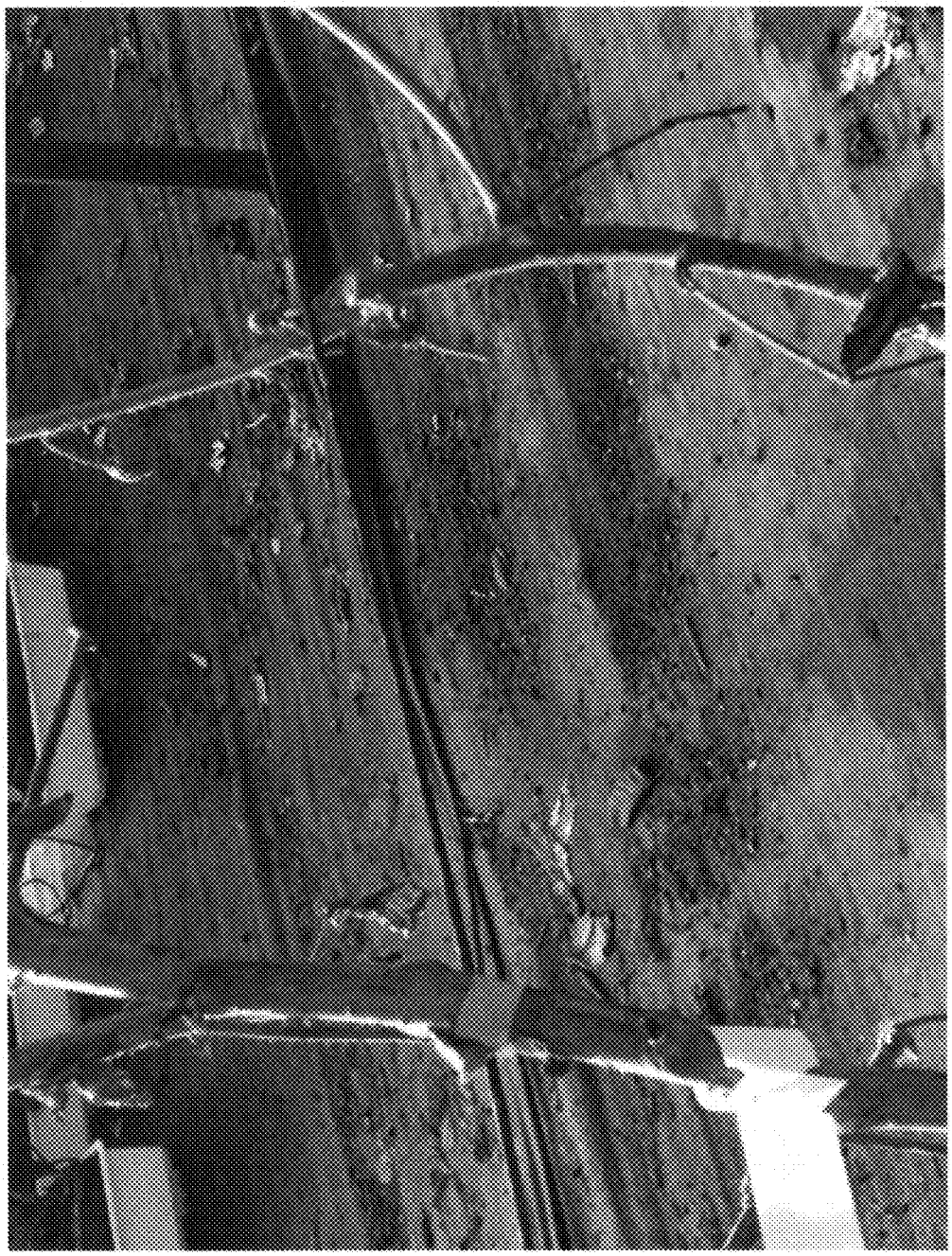
FIG. 12 is a comparison of the shoots of 'Sugana' (left) versus the shoots of 'BP1' (right)
Figure 13:
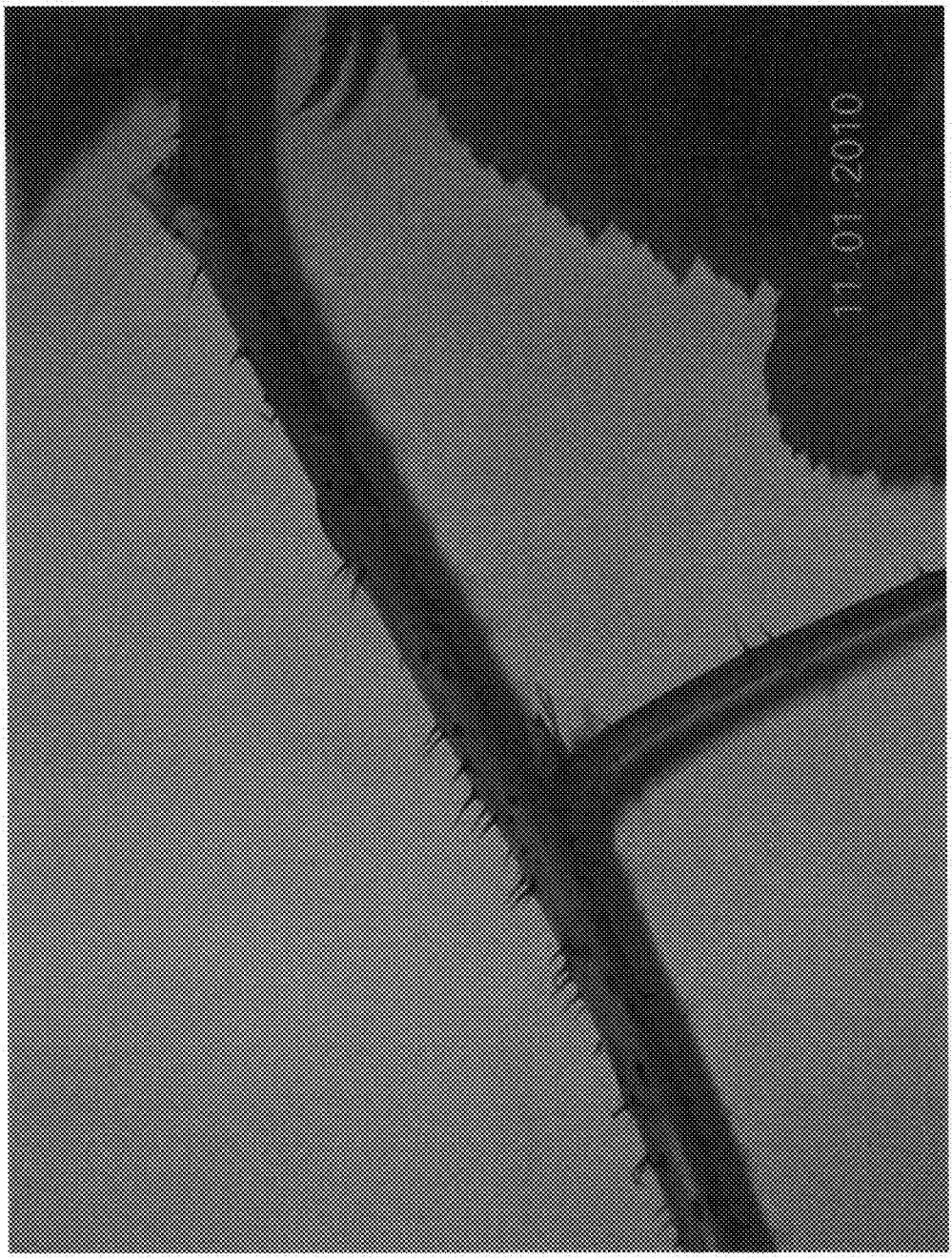
FIG. 13 illustrates a sprout of 'BP1'.

'BP1' has not been observed under all possible environmental conditions. The phenotype may vary somewhat with variations in environment, such as temperature, day length, and light intensity. However, there is no variance in genotype.

In the following description, color references are made to The Royal Horticultural Society Colour Chart (Fifth Edition, 2007), except where general terms of ordinary dictionary significance are used. Two plants of the new variety were planted in a 12 liter pot in a greenhouse tunnel covered with plastic in Verona, Italy, and the plants were approximately 1 year old when described. The measurements were taken under natural light in the greenhouse. Further, unless indicated otherwise, the descriptions herein refer to the primocane.

PLANT

Primary use: 'BP1' is primarily grown for its primocane fruit for fresh market purposes.

Time to initiate roots: 14 days at 18° C., under mist.

Time to produce a rooted plant: 45 days, including acclimatization time.

Rooting habit: Good; young plants typically produce 3-5 roots that branch and fill a 5 cm. container.
Form: Spreading and symmetrical with 3-5 lateral shoots.
Height (from soil to top of plant): 170-180 cm.
Plant diameter: 80-90 cm.
Vigor: Medium.
Disease/pest resistance: None observed to date.
Weather tolerance: As 'BP1' has been protected by a greenhouse environment, no weather tolerance has been observed to date.
Primocane:
*Average number of canes per plant.*—A one-year old plant has 3 canes per plant. Later on, there are at least 3-5 canes.
*Average length.*—170-180 cm.
*Average diameter.*—0.8-1.0 cm.
*Fruiting cane color.*—143D.
*Dormant cane color.*—166A.
*Number of fruiting laterals per cane.*—3-5.
*Internode length.*—5 cm.
*Young shoot color.*—143D.
Thorn:
*Density.*—Medium.
*Length.*—2.5 mm.
*Color.*—166B.
*Texture.*—Relatively hard.
*Tip attitude.*—Downward sloping.
Foliage:
*Arrangement.*—Compound.
*Compound leaf.*—Average length: 15 cm. Average width: 15 cm.
*Number of leaves per stem.*—Usually 3, sometimes 5.
*Fragrance.*—None present.
Petiole:
*Length.*—6 cm.
*Diameter.*—2.5 mm.
*Color.*—145A with 59A thorns.
*Texture.*—Very thin hairs present.
Young leaflet color:
*Upper surface.*—144A.
*Lower surface.*—144B.
Mature leaflet color:
*Upper surface.*—143A.
*Lower surface.*—143B.
Lateral leaflets:
*Length.*—8-9 cm.
*Width.*—5.6-6.0 cm.
*Shape of leaf (generally).*—Ovate.
*Shape of apex.*—Cuspidate.
*Shape of base.*—Cordate.
*Texture.*—Soft.
*Margin type.*—Doubly serrate.
Terminal leaflets:
*Length.*—10-12 cm.
*Width.*—8-9 cm.
*Shape of leaf (generally).*—Ovate.
*Shape of apex.*—Cuspidate.
*Shape of base.*—Cordate.
*Texture.*—Harder and firmer than lateral leaflets.
*Margin type.*—Doubly serrate.
Veins:
*Upper surface color.*—178A.
*Lower surface color.*—178C.
Fruit:
*Harvest season.*—The second week of August until October on primocanes; in June on floricanes.
*Fruit bearing type.*—Both previous years' cane in Summer, and current year's cane in Autumn.
*Number of fruit per fruiting lateral.*—15-25.
*Average number of fruit per node.*—15.
*Average fruit yield per plant.*—180 fruits per cane.
*Immature color.*—43D.
*Maturing color.*—44A.
*Mature color.*—45A.
*Taste.*—Agreeable; similar to 'Tulameen'.
*Length.*—2.8-3.0 cm.; in the mountains the fruit can be more than 3.5 cm. in length.
*Width.*—2.5-2.7 cm.
*Overall shape.*—Conical.
*Glossiness.*—Good; similar to 'Tulameen'.
*Weight.*—5 grams.
*Drupelet size.*—Big to very big; 3 mm. and 0.05 grams.
*Drupelet arrangement.*—Regular.
*Average number of drupelets per fruit.*—100.
*Flesh firmness.*—Good to very good.
*Skin firmness.*—Very good.
*Receptacle/torus length.*—1.8-2.0 cm.
*Receptacle/torus width.*—0.8-0.9 cm.
*Adherence of berry to receptacle.*—The berries are very easy to pick; similar to 'Tulameen'.
*Pubescence.*—Normal.
*Percent soluble solids.*—Average of 8.55.
*Titratable acidity.*—Average of 29.6.
*Penetrometer reading.*—Average of 1.91.
Reproductive organs:
*Pistil number per flower.*—90-120.
*Pistil size.*—Medium; 3 mm.
*Stamen number per flower.*—90-130.
*Stamen size.*—Medium; 4.5 mm.
Flowers:
*Natural flowering season.*—In Verona, Italy, the primocanes of 'BP1' flower from the beginning of August until October, and the floricanes flower at the beginning of May — one week before 'Sugana'.
*Number of flowers per plant.*—180-220.
*Color.*—155D.
*Flower height.*—0.7 cm.
*Flower diameter.*—2.5 cm.
*Pedicel.*—Length: 8 cm. Surface texture: With thorns. Color: 145A.
*Peduncle.*—Length: 4 cm. Surface texture: Smooth, with thorns present. Color: 145A.
*Fragrance.*—None present.
*Longevity.*—Medium.
*Seeds.*—Shape: Bean-like. Length: 2.5 mm. Diameter: 1.0 mm. Color: 20D.

I claim:

1. A new and distinct variety of *Rubus* plant named 'BP1' as herein described and illustrated.

* * * * *